United States Patent [19]
Sanso

[11] Patent Number: 5,289,555
[45] Date of Patent: Feb. 22, 1994

[54] OPTICAL-FIBRE CABLE COUPLER FOR ENDOSCOPE LIGHT SOURCE

[76] Inventor: David W. Sanso, 6598 W. Oregon Ave., Lakewood, Colo. 80226

[21] Appl. No.: 900,969

[22] Filed: Jun. 18, 1992

[51] Int. Cl.$^5$ .......................... G02B 6/00; G02B 6/36
[52] U.S. Cl. ........................................................ 385/92
[58] Field of Search ................. 385/92, 117, 901, 902; 439/191, 595, 924; 128/6; 362/32

[56] References Cited

U.S. PATENT DOCUMENTS

| | | | |
|---|---|---|---|
| 4,770,486 | 9/1988 | Wang et al. | 385/92 |
| 4,824,202 | 4/1989 | Auras | 385/92 X |
| 4,919,621 | 4/1990 | Ams | 385/92 X |
| 4,948,222 | 8/1990 | Corke et al. | 385/92 X |
| 5,179,610 | 1/1993 | Milburn et al. | 385/92 |

Primary Examiner—Akm E. Ullah
Attorney, Agent, or Firm—J. Preston Oxenham

[57] ABSTRACT

An optical-fiber cable coupler for coupling an optical-fiber cable to an endoscope light source includes a heat conducting member which is in heat conductive contact with the end of a sheath of the light source end of an optical-fiber cable so that thermal energy may be drawn from the sheath to the member and flow to a heat sink during illumination of the cable by the light source. In a first embodiment, the heat conducting member is a finger of a collet which is drawn into contact with the sheath by a collet nut. In a second embodiment, the heat conducting member is a resilient, sheath-supporting finger.

18 Claims, 5 Drawing Sheets

OPTICAL-FIBRE CABLE COUPLER FOR ENDOSCOPE LIGHT SOURCE

TECHNICAL FIELD

The present invention relates to light sources for remote illumination. More particularly, the present invention relates to couplers for coupling optical conduits to light sources. Most particularly, the present invention relates to mitigation of heat damage to optical-fibre cables when coupled to and illuminated by endoscope or borascope light sources.

BACKGROUND OF THE INVENTION

Endoscopic procedures are steadily replacing more traditional invasive surgical procedures in contemporary medical practice. During traditional surgical procedures, incisions are required to be sufficiently large to allow direct visual observation of tissues and organs and to allow manipulation of the tissue and organs by a surgeons hands and traditional surgical tools. During an endoscopic procedure, only very small incisions or punctures are made through which catheters and a small diameter endoscope tube are inserted. Light for illumination, and a return visual image of tissues and organs, are conducted through the tube by optical-fibers. Light for illumination is provided by an endoscope light source and is conducted to the endoscope tube through a light conducting conduit, typically a flexible optical-fibre cable.

Generally, as may be seen in FIG. 1, a light source end of an optical-fibre cable 10 is fitted with a metal sheath 20 having locating shoulder 21. Coupling devices of endoscope light sources of the prior art typically include fitting 14, with port 18 sized to receive sheath 20 in a sliding fit, attached to light source cabinet wall 16. Sheath 20 is inserted into light source port 18 until shoulder 21 contacts cooperating shoulder 12 within fitting 14 and sheath 20 is positioned with sheath end 22 protruding from the back of the fitting. Sheath 20 is retained in this position by tightening set screw 15. In this position, light from a light source lamp is focused by lens 17 upon exposed ends of light conducting fibers of cable 10 at protruding end 22 of cable sheath 20 to provide illumination.

In endoscopic light sources of the prior art, extreme heating of the end portion of the sheath and cable occurs during illumination. Adverse effects of this heating of the cable most notably include discoloration and loss of light conducting efficiency at the end portion of the cable over time. This deterioration in cable performance may result from breakdown and scorching of cable bonding materials and optical fiber coatings of the cable. The light source end of the optical-fibre cable is customarily repolished from time to time in a effort to restore performance until the cable must finally be discarded. Extreme heating of the cable and sheath end may also present a burn hazard to operating-room personnel when a cable is removed from a light source without allowing a sufficient cooling time with the light source lamp turned off.

Heating of the light source cable end occurs for a number of reasons. Less efficient light conducting materials in the cable, including bonding and fiber coating materials, convert impinging light energy into heat energy. Focusing of the lamp beam is not perfect, and, consequently, a portion of the focused beam may impinge upon the opaque sheath wall where it contributes to heating of the end portion of the sheath. Electromagnetic radiation from the light source lamp outside the visible spectrum may also impinge upon the end portion of the sheath, further contributing to heat build up.

Attempts have been made to reduce heating of the cable end portion but they have proved ineffective or cumbersome. One light source of the prior art has utilized an air pump and nozzle to direct a stream of cooling air upon the cable end. While this method of cooling has proved effective in reducing heating of the cable end and mitigating deterioration of cable performance over time due to heating, it increases the complexity, weight, size and number of mechanical components of the light source apparatus.

DISCLOSURE OF THE INVENTION

It is an object of the present invention to provide a light source for an endoscope apparatus which will not cause deterioration of optical-fibre cable performance due to heating of the cable.

It is an object of the present invention to provide effective cooling of the light source end of an endoscope optical-fibre cable which is coupled to an endoscope light source.

It is a further object of the present invention to provide an endoscope light source which accomplishes the above objectives without increasing the size, weight, complexity or risk of mechanical failure of the light source.

It is yet a further object of the present invention to provide an optical-fibre cable coupler for an endoscope light source which is quick and easy to operate, mechanically simple and provides positive and effective coupling of the cable to the light source.

In keeping with the above objectives, a light source for an endoscope apparatus comprising a preferred embodiment of the present invention includes an optical-fibre cable coupler having a collet with a central passage sized to receive a cable sheath and extending longitudinally from a cable-receiving end to a cable clamping end of the collet. The collet is fabricated of resilient heat conducting material and has a plurality of fingers extending from a central portion of the collet to free distal ends at the clamping end of the collet. A collet nut has inner screw threads and an inner frusto-conical surface and is fixed to the light source apparatus. A central portion of the collet has outer threads sized to cooperate with the inner threads of the collet nut such that the threads may be engaged and the collet rotated about its longitudinal axis to draw the distal ends of the collet fingers against the frusto-conical surface and cause inner surfaces of the fingers to converge upon a cable sheath within the collet passage and fix the sheath within the passage with the sheath wall in thermal communication with the inside surfaces of the fingers. A locating shoulder in the collet passage cooperates with a locating shoulder of the cable sheath, and the collet fingers are of such a length that, when a sheath is inserted into the passage until the locating shoulders are in abutment, the finger ends generally lie in a common plane with the sheath end.

Other objects, advantages and aspects of the invention will become apparent upon perusal of the following detailed description and claims and upon reference to the accompanying drawings.

DETAILED DESCRIPTION

Figure 1:
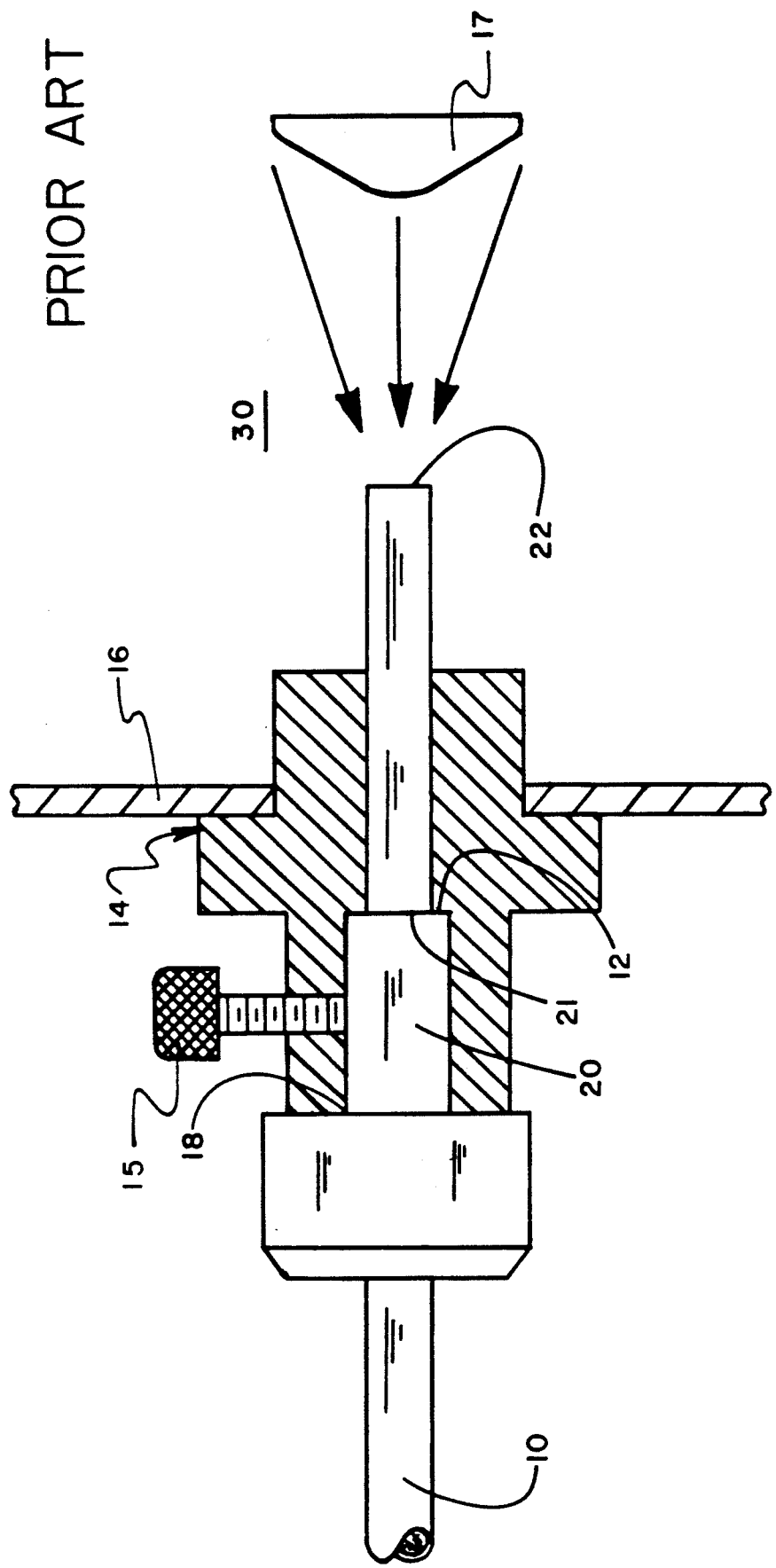
FIG. 1 is a partial sectional view of an optical-fibre cable coupler of an endoscope light source of the prior art with an optical-fibre cable sheath inserted and coupled therein.
Figure 2:
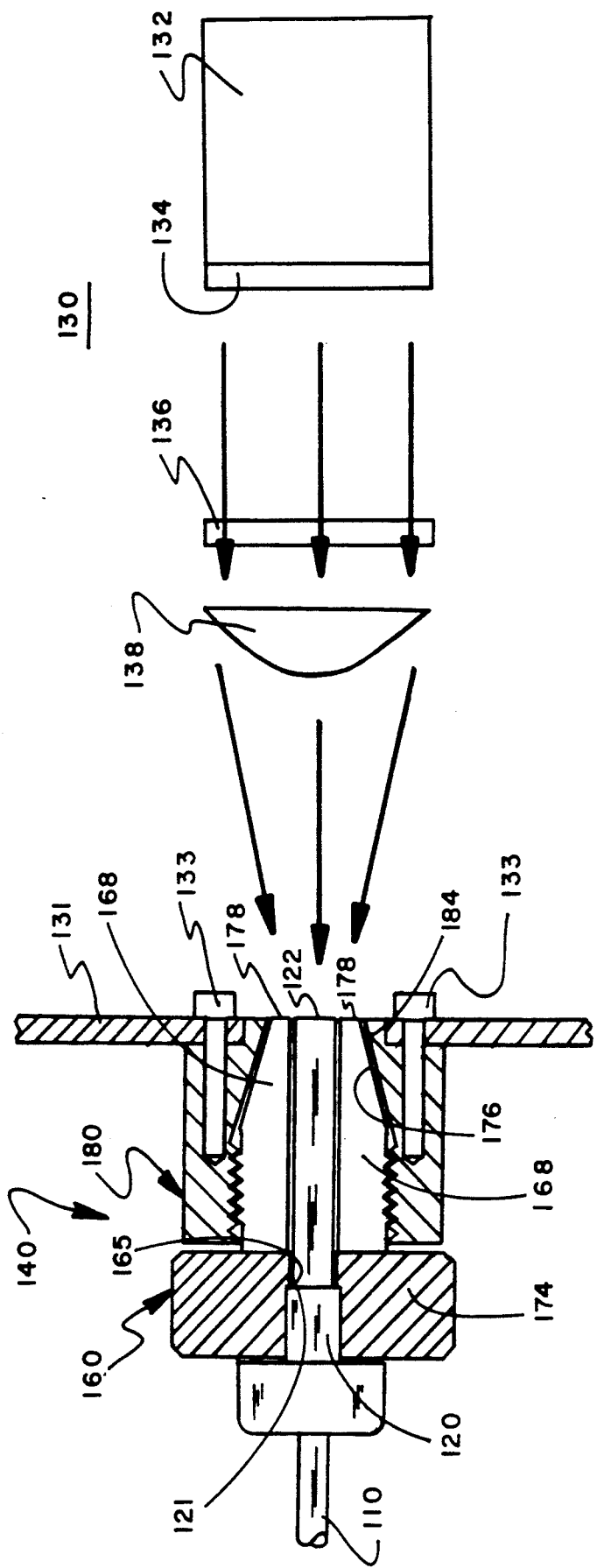
FIG. 2 is a partial sectional view of an optical-fibre cable coupler of an endoscope light source comprising a preferred embodiment of the present invention with an optical-fibre cable sheath inserted and coupled therein.

Exemplary endoscope light source 130 comprising a preferred embodiment of the present invention is shown schematically in FIG. 2 and includes optical-fibre cable coupler 140, shown in section. Optical-fibre cable coupler 140 of exemplary light source 130 comprises collet 160 and collet nut 180. Collet nut 180 is attached to cabinet wall 131 of light source 130 by mounting screws 133.

Figures 3, 4:
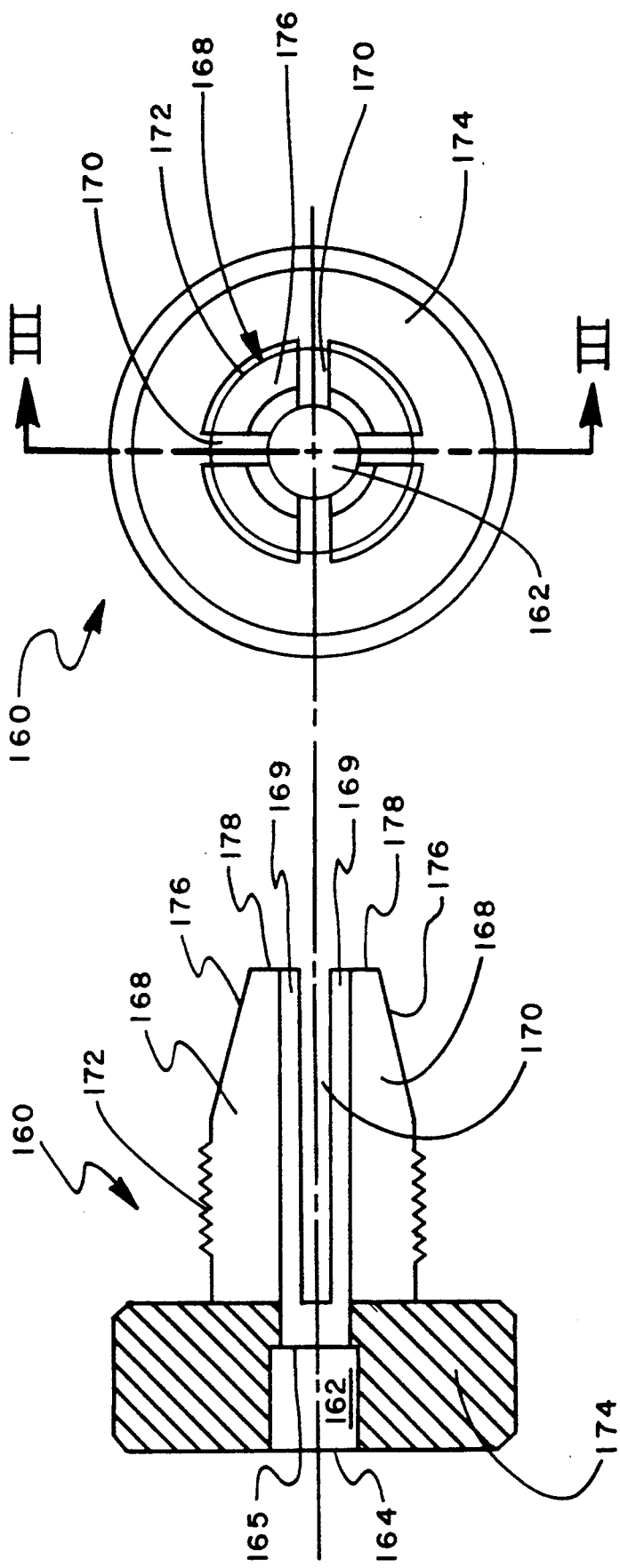
FIG. 3 is a sectional view of a collet of an optical-fibre cable coupler of an endoscope light source comprising a preferred embodiment of the present invention taken at plane III—III of FIG. 4.
FIG. 4 is an end view of a collet of an optical-fibre cable coupler of an endoscope light source comprising a preferred embodiment of the present invention.

As may best be seen in FIGS. 3 and 4, collet 160 of coupler 140 of the preferred embodiment has central passage 162 extending from receiving port 164 to clamping end 166. Locating shoulder 165 is formed in the wall of passage 162. Fingers 168, separated by slots 170, extend from a central portion of collet 160 to free distal ends 178 at clamping end 166 of passage 162. The central portion of collet 160 includes external screw threads 172. Enlarged turning knob 174, for rotating collet 160, is formed at its receiving end. Collet 160 is fabricated of a heat conducting, preferably resilient, material.

Figures 5, 6:
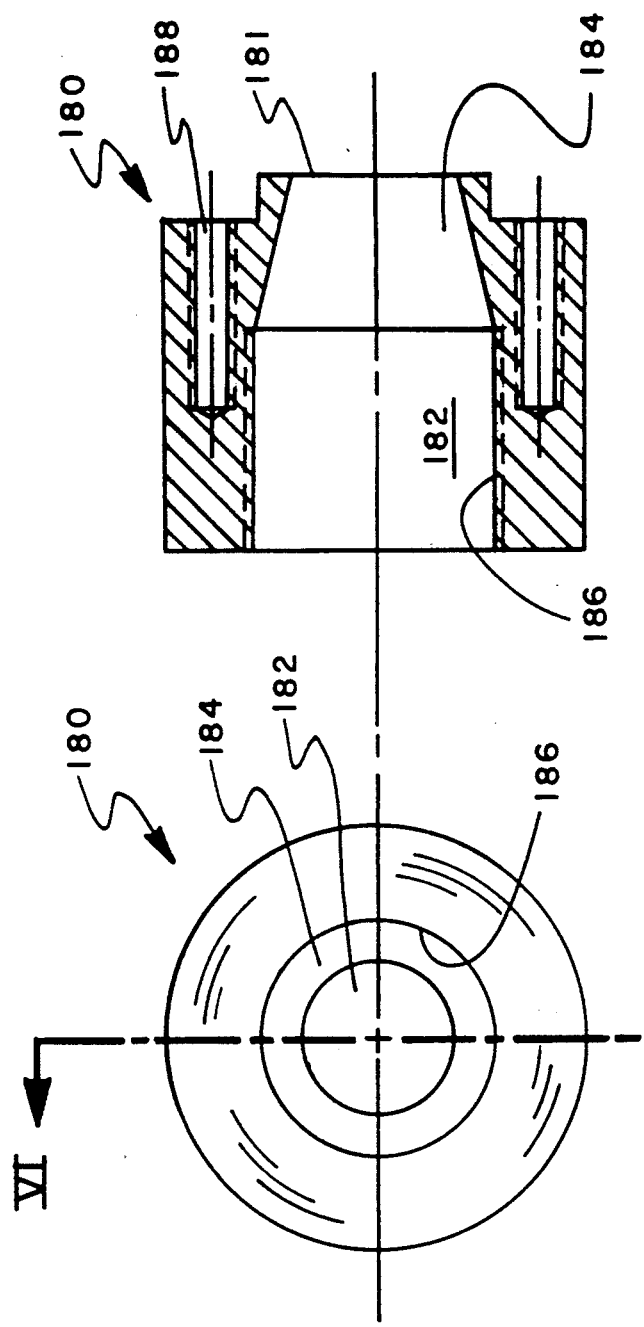
FIG. 5 is an end view of a collet nut of an optical-fibre cable coupler of an endoscope light source comprising a preferred embodiment of the present invention.
FIG. 6 is a sectional view of a collet nut of an optical-fibre cable coupler of an endoscope light source comprising a preferred embodiment of the present invention taken at plane VI—VI of FIG. 5.

As best seen in FIGS. 5 and 6, collet nut 180 of coupler 140 has an inner cavity 182. The inner surface of collet nut 180 includes frusto-conical surface 184 and internal screw threads 186 which are sized to cooperate with external threads 172 of collet 160. Tapped holes 188 are provided to facilitate mounting collet nut 180 on cabinet wall 131 by means of screws 133. Collet nut 180 is preferably fabricated of a heat conducting material.

Sheath 120 of the light source end of optical-fibre cable 110 is shown coupled to exemplary light source 130 comprising the preferred embodiment in FIG. 2. Cable 110 contains light conducting optical-fibers which terminate at polished ends in the plane of sheath end 122. Sheath 120 is typically a metal sheath with locating shoulder 121 formed on its outer surface.

To couple cable 110 to light source 130, sheath 120 is inserted through port 164 into passage 162 of collet 160 such that locating shoulder 121 of sheath 120 is abutting locating shoulder 165 of passage 162 of collet 160. External threads 172 of collet 160 are engaged with internal threads 186 of collet nut 180. Collet 160 is rotated by knob 174 to cause cooperating screw threads 172 and 186 to draw external surfaces 176 of fingers 168 against frusto-conical surface 184 and cause the fingers to move inward toward the center of passage 162 to clamp sheath 120 within passage 162 and establish heat conductive contact between external surface 124 of sheath 120 and internal surfaces 169 of fingers 168. Fingers 168 are preferably of such length, and frusto-conical surface 184 of such size, that distal ends 178 of fingers 168, base surface 181 of collet nut 180, and sheath end 122, lie in a common plane when inner surfaces 169 of fingers 168 are clamping sheath 120 within passage 162 in position for illumination. Slots 170 of the preferred embodiment are carried well back toward knob 174 to maximize contact surface between collet 160 and sheath 120.

During operation of light source 130, as indicated by the arrows in FIG. 2, radiant energy from lamp 132 passes through lamp window 134 and filter 136 and is focused by lens 138 to illuminate exposed ends of light conducting fibers of cable 110 at end 122 of sheath 120. Lamp 132 may be, for example, a 175 watt Xenon lamp with a quartz window, preferably coated to reduce ultraviolet emissions in the light beam. Filter 136 is a dichromic filter which reduces infrared emissions in the light beam. Lens 138 is selected and positioned to focus as much of the light radiated by lamp 132 as practicable upon the exposed optical-fibre ends at sheath end 122.

With the sheath properly secured in coupler 140 and illuminated, heat created in sheath 120 adjacent end 122 flows through the sheath wall into fingers 168 of collet 160. From fingers 168, the heat flows to other portions of collet 160, into collet nut 180 and cabinet wall 131. As these heat sinks warm, the heat passes from their larger surface areas to the ambient atmosphere before excessive warming occurs. Heating of the sheath is further mitigated by shading of the sheath wall by fingers 168 as light impinges upon distal ends 178 of fingers 168 and base surface 181 of the collet nut 180 rather than impinging upon the external surface of the sheath 120 and warming the sheath. Fingers 168 of the preferred embodiment are made of a resilient material such that, when knob 174 is turned to cause external finger surfaces 176 to be withdrawn from contact with frusto-conical surface 184, sheath 120 may be slid easily from passage 162.

Figure 7:
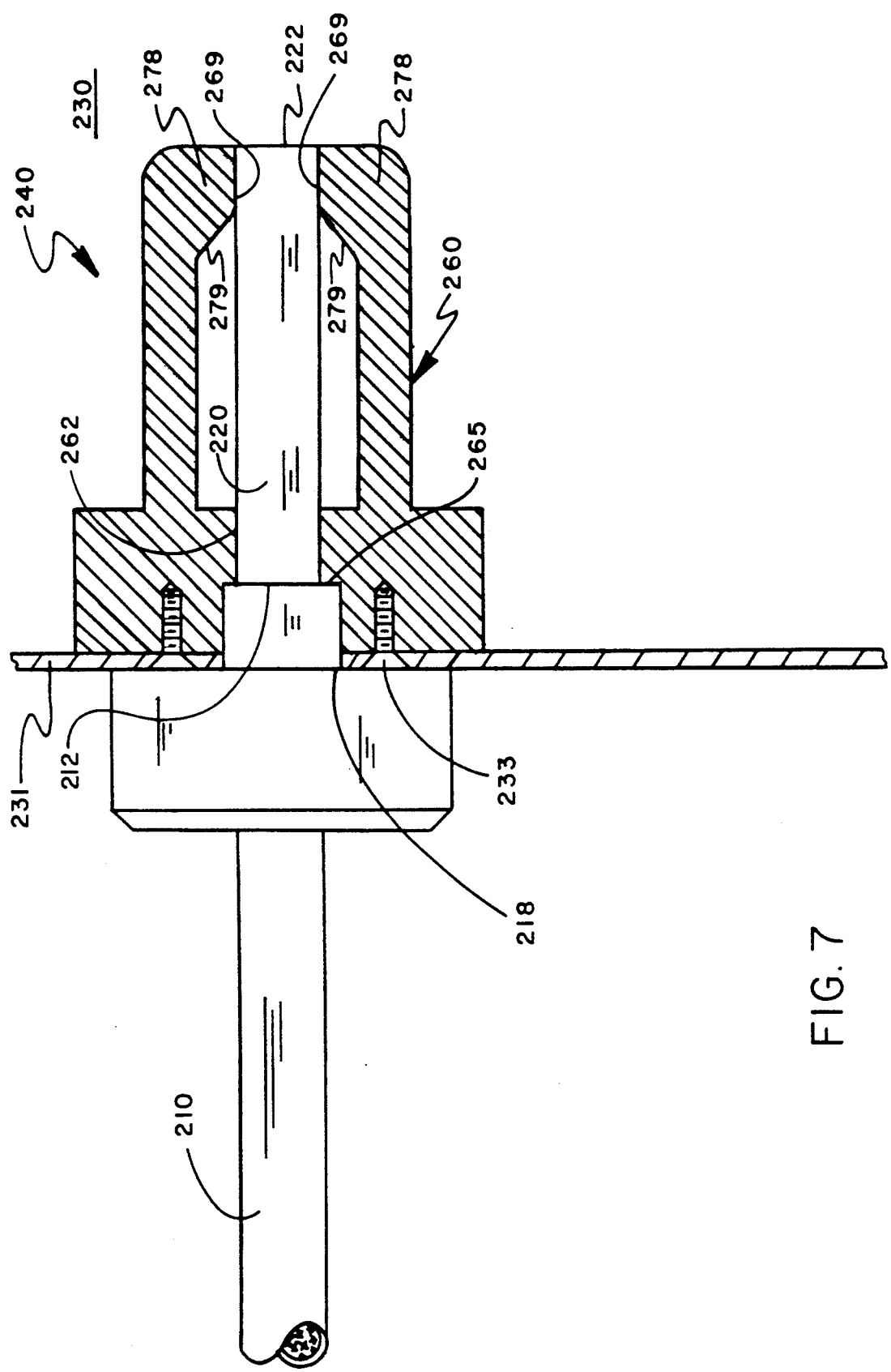
FIG. 7 is a partial sectional view of an optical-fibre cable coupler of an endoscope light source comprising an alternative embodiment of the present invention with an optical-fibre cable sheath inserted and coupled therein.

Exemplary endoscope light source 230 comprising an alternative embodiment of the present invention is shown schematically in FIG. 7 and includes optical-fibre cable coupler 240, shown in section. Collet 260 of coupler 240 is mounted upon wall 231 of light source 230 by mounting screws 233. Fingers 268 of coupler 240 are made of resilient, heat conducting material and extend to free distal ends 278. Fingers 268 are shaped such that interior surfaces 269 of fingers 268 define a passage portion smaller than the diameter of the exterior surface of sheath 220 adjacent sheath end 222. Thus, as sheath 220 is inserted through entry port 264 into passage 262, sheath end 222 strikes angled finger surfaces 279, displacing distal ends 278 of fingers 268 outward. When sheath 220 is fully inserted with locating shoulder 212 abutting shoulder 265 of passage 262, inner finger surfaces 269 are resiliently biased against the outer sheath wall adjacent sheath end 222 and heat is conducted from the sheath end by heat conducting fingers 268 when end 222 is illuminated. In the embodiment of FIG. 7, fingers 286 are formed such that sufficient friction occurs between interior surfaces 269 and the sheath wall to retain sheath 220 correctly located within passage 262. If more positive retention is required, a detent or friction lock mechanism may be made integral with coupler 240.

While exemplary light sources comprising embodiments of the present invention have been shown, it will be understood, of course, that the invention is not limited to those embodiments. Modification may be made by those skilled in the art, particularly in light of the foregoing teachings. For example, while the sheath end, distal finger ends and base surface of the collet nut of the preferred embodiment described above generally lie in a common plane when the sheath is inserted and in proper position for illumination, the distal finger ends may be made to extend beyond the sheath end to shade the edge of the sheath wall. It is, therefore, contemplated by the appended claims to cover any such modification which incorporates the essential features of this invention or which encompasses the spirit and scope of the invention.

I claim:

1. A coupler for coupling an optical-fibre cable to an endoscope light source comprising:
   a collet extending along a central axis from a cable receiving end to a cable clamping end and surrounding a central passage sized to slidingly receive a sheath of a light source end of the optical-fibre cable, said collet comprising a heat conductive finger with an inner heat-conducting surface, the finger extending from a central portion of said collet between said receiving end and said clamping end toward said clamping end; and,
   means for causing heat conducting contact of said inner heat-conducting surface of said finger with a cable sheath lying within said passage.

2. A coupler, as in claim 1, in which said contact causing means comprises:
   resilient biasing means for biasing said inner heat-conducting surface of said finger against an exterior surface of the cable sheath when the cable sheath is inserted into said passage.

3. A coupler, as in claim 2, in which said biasing means comprises said finger extends inward toward said central axis and includes a resilient material such that said finger is displaced resiliently outward and away from said central axis by the sheath when inserted in said passage.

4. A coupler, as in claim 3, comprising a plurality of said fingers.

5. A coupler, as in claim 4, further comprising a locating shoulder within said passage for locating a sheath longitudinally at a predetermined position along said central axis when the sheath is inserted into said passage and said fingers are of a length such that said distal ends are generally even with an end of the sheath when the sheath is located in said predetermined position.

6. A coupler, as in claim 1, in which said finger extends to a free distal end and said contact causing means comprises a collet nut surrounding a cavity, the cavity defined by a collet-nut inner surface including a converging portion and means for moving said collet relative to said collet nut longitudinally along said collet axis to force an outside surface of said finger against said converging portion of said collet-nut inner surface and cause said finger inner surface to move toward said collet axis.

7. A coupler, as in claim 6, in which said converging portion is a frusto-conical surface surrounding a central axis and said collet moving means comprises screw threads formed on an outer surface of said collet and cooperating screw threads formed on said inner surface of said collet nut such that said distal end may be drawn toward said frusto-conical surface by relative rotation of said collet and said collet nut.

8. A coupler, as in claim 7, comprising a plurality of said fingers.

9. A coupler, as in claim 8, further comprising locating means for locating a sheath longitudinally at a predetermined position along said central axis when the sheath is inserted into said passage and said fingers are of a length such that said distal ends are generally even with an end of the sheath when the sheath is located in said predetermined position.

10. A coupler, as in claim 9, in which said locating means comprises a locating shoulder within said passage.

11. A coupler, as in claim 7, in which said finger comprises a resilient material.

12. A coupler, as in claim 1, further comprising locating means for locating a sheath longitudinally at a predetermined position along said central axis when the sheath is inserted into said passage and said finger extends to a free distal end and is of a length such that said distal end is generally even with an end of the sheath when the sheath is located in said predetermined position.

13. A coupler as in claim 6, in which said collet nut is fabricated of heat conductive material.

14. A coupler as in claim 1, in which said collet comprises a heat conductive path from said inner finger surface to a heat sink.

15. An endoscope light source comprising:
   illumination means for illuminating a light source end of an optical-fibre cable;
   positioning means for retaining a sheath of a light source end of the optical-fibre cable in a predetermined location for illumination; and,
   a heat conducting member for heat conductive contact with an end portion of the sheath while it is illuminated such that thermal energy may be drawn from the sheath to the member during illumination.

16. An endoscope light source, as in claim 15, further comprising a heat sink in thermal communication with said heat conducting member.

17. An endoscope light source, as in claim 15, in which said positioning means retains the sheath with a sheath axis lying along a predetermined axis and further comprising:
   a plurality of heat conductive members about said axis; and,
   means for urging said members radially toward said axis to bring said members into heat-conducting contact with the sheath.

18. An endoscope light source, as in claim 17, in which said positioning means comprises said members.

* * * * *